(12) United States Patent
Teng

(10) Patent No.: US 10,080,720 B2
(45) Date of Patent: *Sep. 25, 2018

(54) PHARMACEUTICAL COMPOSITION CONTAINING DOCETAXEL

(71) Applicants: GAINIA (SHANGHAI) PATENT TECHNOLOGY LTD., Shanghai (CN); POLYMER CHEMICAL CO. LTD, Shanghai (CN)

(72) Inventor: Xin Teng, Shanghai (CN)

(73) Assignees: GAINIA (SHANGHAI) PATENT TECHNOLOGY LTD., Shanghai (CN); POLYMER CHEMICAL CO. LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/325,939

(22) PCT Filed: Jul. 14, 2015

(86) PCT No.: PCT/CN2015/083928
§ 371 (c)(1),
(2) Date: Jan. 12, 2017

(87) PCT Pub. No.: WO2016/008401
PCT Pub. Date: Jan. 21, 2016

(65) Prior Publication Data
US 2017/0157050 A1    Jun. 8, 2017

(30) Foreign Application Priority Data

| Jul. 15, 2014 | (CN) | 2014 1 0336415 |
| Jul. 15, 2014 | (CN) | 2014 1 0336424 |
| Jul. 15, 2014 | (CN) | 2014 1 0336464 |
| Jul. 15, 2014 | (CN) | 2014 1 0336638 |

(51) Int. Cl.
| *A61K 9/14*   | (2006.01) |
| *A61K 9/19*   | (2006.01) |
| *A61K 31/337* | (2006.01) |
| *A61K 47/34*  | (2017.01) |
| *A61K 9/00*   | (2006.01) |
| *A61K 9/107*  | (2006.01) |

(52) U.S. Cl.
CPC ............ *A61K 9/146* (2013.01); *A61K 9/0019* (2013.01); *A61K 9/1075* (2013.01); *A61K 9/19* (2013.01); *A61K 31/337* (2013.01); *A61K 47/34* (2013.01)

(58) Field of Classification Search
CPC ......... A61K 31/337; A61K 9/146; A61K 9/19
See application file for complete search history.

(56) References Cited

U.S. PATENT DOCUMENTS

| 9,499,667 B2* | 11/2016 | Gu ............... A61K 47/48215 |
| 2007/0104654 A1 | 5/2007 | Hsieh et al. |
| 2009/0220604 A1 | 9/2009 | Gravett |
| 2011/0274759 A1* | 11/2011 | Troiano ............... A61K 9/10 |
| | | 424/489 |

FOREIGN PATENT DOCUMENTS

| CN | 1429120 A     | 7/2003  |
| CN | 200780000695.1 | 2/2007 |
| CN | 101330912 A   | 12/2008 |
| CN | 201010151501.1 | 4/2010 |
| CN | 101787119 A   | 7/2010  |
| CN | 101804021 A   | 8/2010  |
| CN | 101869712 A   | 10/2010 |
| CN | 101330912 B   | 12/2010 |
| CN | 101972480 A   | 2/2011  |
| CN | 101804021 B   | 5/2012  |
| CN | 102617843 A   | 8/2012  |
| CN | 201210372072.X | 9/2012 |
| CN | 102885772 A   | 1/2013  |
| CN | 102885772 B   | 11/2013 |
| CN | 103772686 A   | 5/2014  |
| CN | 104510703 A   | 4/2015  |
| CN | 104510705 A   | 4/2015  |
| CN | 104510706 A   | 4/2015  |

(Continued)

OTHER PUBLICATIONS

Wu Yi, et al, "Pharmacology, pharmacokinetics Research and Analysis Methods 80 pharmaceutical excipients Twain", Chinese medicine thing, 2008, vol. 22, No. 8, 5 pgs. with Abs.

(Continued)

*Primary Examiner* — Anna R Falkowitz
(74) *Attorney, Agent, or Firm* — Muncy, Geissler, Olds & Lowe, P.C.

(57) ABSTRACT

The present invention is a technical filed of pharmaceutical preparation agent, and more particular to a pharmaceutical composition containing docetaxe. The pharmaceutical composition containing docetaxe includes docetaxel and a polyethylene glycol methyl ether-polylactide block copolymer with amino acid end groups. The advantage of the present invention is subjected to a tri-block copolymer with low toxicity as the drug carrier. In addition to the pharmaceutical active ingredients and carrier, there is no other additive in pharmaceutical composition containing docetaxe. Thus, the prescription is simpler and the security is higher. In pharmaceutical component containing docetaxel, docetaxel content is more than 20%, such that the preparation process of pharmaceutical component containing docetaxel is simple, and easy for the industrial applications.

5 Claims, No Drawings

(56) References Cited

FOREIGN PATENT DOCUMENTS

| CN | 104510712 A | 4/2015 | | |
|---|---|---|---|---|
| CN | 104510713 A | 4/2015 | | |
| CN | 104510714 A | 4/2015 | | |
| CN | 104510715 A | 4/2015 | | |
| CN | 104510716 A | 4/2015 | | |
| CN | 104511020 A | 4/2015 | | |
| CN | 104511021 A | 4/2015 | | |
| CN | 104511022 A | 4/2015 | | |
| CN | 104511023 A | 4/2015 | | |
| CN | 104511024 A | 4/2015 | | |
| CN | 104546708 A | 4/2015 | | |
| CN | 104546740 A | 4/2015 | | |
| WO | WO 2011/011978 | * | 2/2011 | ............... A61K 9/16 |
| WO | WO 2011/011978 A1 | 2/2011 | | |

OTHER PUBLICATIONS

Sun Li, et al, "Tween-80 cause allergic reactions animal preliminary exploration", J. Toxicology, Aug. 2007, vol. 21, No. 4, 3 pgs.

* cited by examiner

PHARMACEUTICAL COMPOSITION CONTAINING DOCETAXEL

CROSS-REFERENCE TO RELATED APPLICATIONS

This application claims the benefit of priority under 35 U.S.C. § 119(e) to China Patent application No. 201410336464.x filed on Jul. 15, 2014, China Patent Application No. 201410336638.2 filed on Jul. 15, 2014, China patent application No. 201410336424.5 filed on Jul. 15, 2014, and China Patent Application No. 201410336415.6 filed on Jul. 15, 2014. The aforementioned patent application is incorporated herein by reference in its entirety.

FIELD OF THE INVENTION

The present invention relates to a technical field of pharmaceutical preparation, particularly relates to a pharmaceutical composition containing docetaxel.

BACKGROUND OF THE INVENTION

Docetaxel (docetaxel, Docetaxel, $C_{43}HS_3NO_{14}$) is based on the structure of a natural anticancer drug taxol, which is a novel anticancer drugs obtained after structural modification. The resistance spectrum of docetaxel and paclitaxel are similar. The mechanism of docetaxel is to promote tubulin polymerization and prevent microtubule depolymerization, thereby the mitosis and proliferation of the cancer cell is to be inhibited, and the efficacy of docetaxel is better than that of paclitaxel.

In vitro studies show that the cell lines in the human breast, colon, bladder, and epithelial with IC50 is less than 9 times paclitaxel. In vivo studies suggest that docetaxel has a high degree of anti-tumor activity, after treatment and transplanted tumors in mice; murine tumor can be completely dissipated. More importantly, docetaxel to paclitaxel-resistant cell line does not spontaneously produce docetaxel cross-resistance.

Docetaxel is white or almost white powder which is a drug with highly fat-soluble and insoluble in water. The solubility of docetaxel in water is 6-7 µg/ml. In order to increase the solubility of docetaxel, the currently commercial formulation of docetaxel are required to add Tween-80 as a surfactant. The use of Tween 80 has two major drawbacks.

The first drawback is that the strong adverse reaction is brought to patients. Tween-80 may cause adverse reaction that includes allergic reactions, hemolysis, cardiovascular adverse reactions and fluid retention. The publication document has been published such as Tween-80 cause allergic reactions animal preliminary exploration, Toxicology 2007, 04, and Pharmacology, pharmacokinetics Research and Analysis Methods 80 pharmaceutical excipients Twain, Chinese medicine thing, 2008, Vol. 22, No. 8. Therefore, the patients need to the oral glucocorticoids drug desensitization in advance. Accordingly, an allergies reaction has been occurred in patients that need to injection of epinephrine, which will undoubtedly increase the burden on patients.

The second drawback is that the administration method is more complex, more difficult to use. Take Taxotere as an example, the concentration drug is mixed with the dilution to prepare the pre-mixed solution, and then the pre-mixed solution is diluted with 0.9% physiological saline solution to prepare the pre-mixed dilution. Within 4 hours, the pre-mixed dilution is infused for 1 hour. In infusion process, the concentration drug mixed with the dilution requires to upside down carefully about 45 seconds but did not require stirring. The bubbles might be generated in the resulted solution, such that the resulted solution is standing for 5 minutes to discharge the bubbles. The docetaxel injection product, Docetaxel, is produced by Qilu pharmaceutical production. The specification has the following caption: "the labeled amount of each bottle is 1 ml: 20 mg of docetaxel; the actual docetaxel solution is filled with 1.2 ml of 20 mg/ml, equivalent to 24 mg of docetaxel. This volume is used for the supplement for the volume lost due to the viscous liquid is adhered on the bottle wall, and the amount of the liquid cannot be withdrawn from the bottle which is called "dead volume". During operation, a syringe extracts docetaxel from the bottle and dilutes to 5% glucose injection solution or 0.9% sodium chloride injection solution. In order to avoid the drug overdose toxicity, the vial and syringe cannot be rinsed by solvent The polymer micelle with nanoscale particle size is a core-shell structure which is spontaneously formed by amphiphilic block copolymers. The polymer micelle is used as an administration carrier that is firstly proposed by Bader et al in 1984. The amphiphilic block copolymer encapsulated the drug within a hydrophobic core of the polymer micelle to achieve the solubility of insoluble drugs and further improve the bioavailability effect. In addition, good polymeric micelles can prolong the drug circulation time in the human body, reduce the toxicity, and through the EPR effect so as to reach the passive targeting.

The docetaxel micelle which is made by polymer micelles can overcome the drawbacks of commercially available docetaxel agents. However, the research result for the docetaxel micelle lacks of practical value, the major drawbacks include the particle size is too large to play the EPR effect, lower drug loading, the poor stability of the preparation. For example, in Shandong University, KeWei Yu utilizes Pluronic F68 as a micelle carrier, vitamin ETPGS as a solubilizer to encapsulate the docetaxel, such that the average drug loading of the prepared docetaxel micelle only 0.923%. The average particle diameter of the prepared docetaxel micelle is up to 135.1±3.42 nm (Docetaxel polymeric micelles research by KeWei Yu). In Shandong University, Zhai et al utilize TPGS, MPEG-PLA, CSO-SA as a micelles carrier material to obtain the docetaxel micelles, and the drug loading does not exceed 5.2%, the entitled as "a docetaxel mixed micelles and preparation method contained, China patent application No. 201210372072.X).

The freeze-dried powder is an effective way to deposit the drug. The product is dried at low temperatures so that the moisture contained in the product is to be frozen, and then the product is placed in a vacuum environment to be dried, so as to the water is directly sublimed from a solid state to vapor and is excluded from the product, such that the product activity is dried. This method effectively prevents the change of the physicochemical and biological properties of the product, and effectively to protect the stability of the heat-sensitive pharmaceutical active ingredient. The freeze-dried powder in the form of loose after drying, and the colors of the freeze-dried powder basically does not change. The freeze-dried powder can quickly dissolve with water or a hydrophilic organic solvent and restore the physical and chemical properties and biological activity for the original aqueous solution. Because the freeze-dried powder is dried under vacuum conditions, for some easily oxidized substance has a good protective effect. The moisture content of freeze-dried powder product after lyophilization procedure is very low, so that the stability of freeze-dried powder product is increased, and the chance of contamination is to be decreased. Therefore, the preparation method is not only convenient transportation also extended the shelf life of the product.

At present, the research result for the docetaxel freeze-dried powder did not achieve a breakthrough, especially in the components, the particle size after reconstitution and the amount of drug loading and so on. ShouZhu Hao published a method for preparing docetaxel lyophilized powder (the entitled as "A docetaxel pharmaceutical composition, preparation method and use", China Patent application No. 200780000695.1), and the disclosure of ShouZhu Hao still contains a freeze-dried powder spit temperature 80. Shandong University, Zhang Na et al utilize PLA-PEG copolymer micelles to obtain the docetaxel freeze-dried powder, but the particle size of the docetaxel freeze-dried powder after reconstitution is greater than 200 nm or more (The entitled as "preparation contained docetaxel nanoparticles mixed micelles and the freeze-drying agent", China Patent application No. 201010151501.1).

SUMMARY OF THE INVENTION

The objective of the present invention is to overcome the drawbacks of the prior art. The present invention provides a pharmaceutical compositions containing docetaxel. The pharmaceutical composition of the present invention is manufactured by polyethylene glycol methyl ether-polylactide block copolymer with amino end groups as the carrier material and docetaxel. The prescription of pharmaceutical composition is simple, safe and reliable. The amount of drug loading for docetaxel in pharmaceutical composition can exceed 25%. The particle size of the freeze-dried powder is small after reconstitution small and having high stability.

The technical solutions of the present invention are described as follows.

The pharmaceutical composition containing docetaxel is manufactured by polyethylene glycol methyl ether-polylactide block copolymer with amino acid end groups and docetaxel, in which the chemical structure of polyethylene glycol methyl ether-polylactide block copolymer with amino end groups as follows

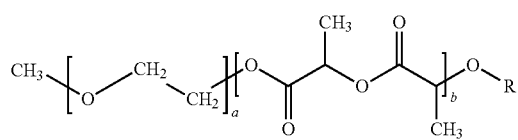

(I)

In the chemical formula (I), the functional group R is an amino acid group, the subscript a is ranging from 10-200, the subscript b is ranging from 3-30, the average molecular weight of polyethylene glycol methyl ether is selected from the group consisting of 1017~2992, 987~3020, 998~2998, and 1003~3015, the average molecular weight of polylactide block copolymer is selected from the group consisting of 505~4892, 495~4996, 502~4962, and 505~4985, the component of docetaxel is ranging from 3.21-27.75 by weight, and the component of polyethylene glycol methyl ether-polylactide block copolymer with amino acid end groups is 100 by weight.

In the above formula (I), the functional group R is amino acid group and chemical structure is

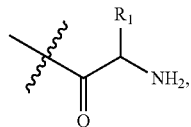

in which the functional group $R_1$ is H, $CH_3$, $(CH_3)_2CH$, $PhCH_2$ or $(CH_2)_3NHC(NH)NH_2$.

Polyethylene glycol methyl ether of polyethylene glycol methyl ether-polylactide block copolymer with amino acid end groups that having higher stability and is less prone to be degradated. Polylactide block copolymer of polyethylene glycol methyl ether-polylactide block copolymer with amino acid end groups is degradated only under strong acid conditions. The graft amino acid is reacted under neutral conditions. Therefore, the stability of polyethylene glycol methyl ether-polylactide block copolymer with amino acid end groups is higher under normal solution environment. The average molecular weight of the different tri-blocks for polyethylene glycol methyl ether and polylactide block copolymer of polyethylene glycol methyl ether-polylactide block copolymer with amino acid end groups is obtained by mass spectrometry analysis.

The aforementioned pharmaceutical composition containing docetaxel is a freeze-dried powder, which is manufactured by lyophilization method.

The docetaxel of the present invention is anhydrous docetaxel, and the purity of docetaxel is counted according to chemical formula, $C_{43}H_{53}NO_{14}$, the purity of docetaxel is more than 98.0%.

The study of the present invention shows that polyethylene glycol methyl ether-polylactide block copolymer with amino acid end groups having no significant carcinogenic, no reproductive toxicity, teratogenic, or mutagenic. The polyethylene glycol methyl ether-polylactide block copolymer with amino acid end groups is to be degradated as latic acid or amino PEG in human body and can be directly discharged from the human body. The present invention is subjected to acute toxicity tests within mice, LD50>2.00 g/kg in mice. During the long-term toxicity test, the dose was 1.00 g/kg, 1 time/day, continuing administrated for 2 days a week. Then, stopping administrated 5 days. Next, continuing administrated for 13 weeks, and restoring for 4 weeks for observation. The results show that there are no significant side effects in mice.

By cytotoxicity tests show that cytotoxicity of tri-block copolymers is lower than that of mPEG-PLA block copolymer, and mPEG-PLA block copolymer is well-known non-toxicity copolymer currently, in which Table 1 to Table 4 respectively shows the results for polyethylene glycol methyl ether-polylactide block copolymer with different amino acid end groups by using MTT assay hepatotoxicity test.

TABLE 1

| Hepatocyte toxicity test results by MTT method: Polyethylene glycol methyl ether-polylactide-lysine | | | | |
|---|---|---|---|---|
| | Polyethylene glycol methyl ether-polylactide-lysine | | mPEG-PLA | |
| Concentration µg/mL | Cell viability % | error % | Cell viability % | error % |
| 0 | 100 | ±3.23 | 96 | ±4.22 |
| 10 | 99.72 | ±6.53 | 91.24 | ±3.25 |

TABLE 1-continued

Hepatocyte toxicity test results by MTT method: Polyethylene glycol methyl ether-polylactide-lysine

| Concentration | Polyethylene glycol methyl ether-polylactide-lysine | | mPEG-PLA | |
|---|---|---|---|---|
| µg/mL | Cell viability % | error % | Cell viability % | error % |
| 100 | 98.95 | ±2.32 | 93.41 | ±4.77 |
| 250 | 97.23 | ±3.51 | 90.07 | ±3.34 |
| 500 | 97.16 | ±2.53 | 85.45 | ±5.72 |
| 1000 | 96.31 | ±2.34 | 76.28 | ±5.28 |

TABLE 2

Hepatocyte toxicity test results by MTT method: Polyethylene glycol methyl ether-polylactide-aspartate

| Concentration | Polyethylene glycol methyl ether-polylactide-aspartate | | mPEG-PLA | |
|---|---|---|---|---|
| µg/mL | Cell viability % | error % | Cell viability % | error % |
| 0 | 100 | ±3.23 | 96 | ±4.22 |
| 10 | 99.72 | ±6.53 | 91.24 | ±3.25 |
| 100 | 98.95 | ±2.32 | 93.41 | ±4.77 |
| 250 | 97.23 | ±3.51 | 90.07 | ±3.34 |
| 500 | 97.16 | ±2.53 | 85.45 | ±5.72 |
| 1000 | 96.31 | ±2.34 | 76.28 | ±5.28 |

TABLE 3

Hepatocyte toxicity test results by MTT method: Polyethylene glycol methyl ether-polylactide-glutamic acid

| Concentration | Polyethylene glycol methyl ether-polylactide-glutamic acid | | mPEG-PLA | |
|---|---|---|---|---|
| µg/mL | Cell viability % | error % | Cell viability % | error % |
| 0 | 100 | ±3.23 | 96 | ±4.22 |
| 10 | 99.72 | ±6.53 | 91.24 | ±3.25 |
| 100 | 98.95 | ±2.32 | 93.41 | ±4.77 |
| 250 | 97.23 | ±3.51 | 90.07 | ±3.34 |
| 500 | 97.16 | ±2.53 | 85.45 | ±5.72 |
| 1000 | 96.31 | ±2.34 | 76.28 | ±5.28 |

TABLE 4

Hepatocyte toxicity test results by MTT method: Polyethylene glycol methyl ether-polylactide-phenylalanine

| Concentration | Polyethylene glycol methyl ether-polylactide-phenylalanine | | mPEG-PLA | |
|---|---|---|---|---|
| µg/mL | Cell viability % | error % | Cell viability % | error % |
| 0 | 100 | ±3.23 | 96 | ±4.22 |
| 10 | 99.72 | ±6.53 | 91.24 | ±3.25 |
| 100 | 98.95 | ±2.32 | 93.41 | ±4.77 |
| 250 | 97.23 | ±3.51 | 90.07 | ±3.34 |
| 500 | 97.16 | ±2.53 | 85.45 | ±5.72 |
| 1000 | 96.31 | ±2.34 | 76.28 | ±5.28 |

To compared with the prior art, the advantageous effects of present invention as follows:

1. The present invention is subjected to polyethylene glycol methyl ether-polylactide block copolymer with amino acid end groups with low toxicity as the drug carrier, in addition to the pharmaceutical active ingredients and carrier, there is no other additives in polyethylene glycol methyl ether-polylactide block copolymer with amino acid end groups. Thus, the prescription is simpler and the security is higher.

2. The composition may be manufactured by lyophilization process for the pharmaceutical industry to form the solid freeze-dried powder. The solid freeze-dried powder can be quickly redissolved in the physiological saline, water for injection or glucose for injection, so that the preparation, transport, storage and use for the drug are more convenient.

3. In pharmaceutical component containing docetaxel, docetaxel content is more than 20%, such that the preparation process of pharmaceutical component containing docetaxel is simple, and easy for the industrial applications.

DETAILED DESCRIPTION OF THE PREFERRED EMBODIMENT

Some embodiments of the invention will now be described in greater detail. Nevertheless, it should be recognized that the present invention can be practiced in a wide range of other embodiments besides those explicitly described, and the scope of the present invention is expressly not limited except as specified in the accompanying claims. The following materials, reagents, and like are used in the following embodiment, if no special instructions, the material, reagents can be obtained from the commercial way.

In the present invention, the formula of polyethylene glycol methyl ether-polylactide block copolymer with amino acid end groups as follows:

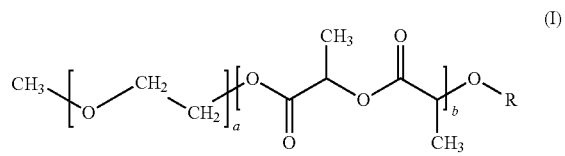

In the chemical formula (I), the functional group R is an amino acid, the subscript a is ranging from 10-200, the subscript b is ranging from 3-30, the average molecular weight of polyethylene glycol methyl ether is selected from the group consisting of 1017~2992, 987~3020, 1003~301, and 998~2998, and the average molecular weight of polylactide block is selected from the group consisting of 505~4892, 495~4996, 504~4985, and 502~4962.

In formula (I), the functional group R is amino group and the chemical structure is

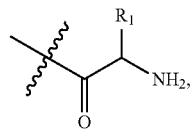

wherein the functional group $R_1$ is H, $CH_3(CH_3)_2CH$, $PhCH_2$ or $(CH_2)_3NHC(NH)NH_2$.

Examples 1-7

Docetaxel is anhydrous docetaxel (CAS: 114977-28-5), which is produced by Xi'an Tianfeng natural field Bio-Technique Co., Ltd.

In Examples 1-7, polyethylene glycol methyl ether-polylactide block copolymer with amino acid end groups is polyethylene glycol methyl ether-polylactide-lysine, and the chemical formula of polyethylene glycol methyl ether-polylactide-lysine as follows:

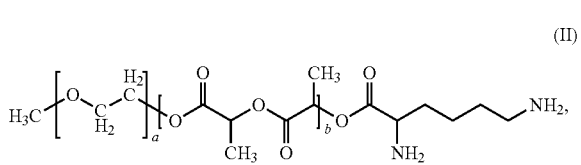

wherein the subscript a in formula (II) is ranging from 10-200, the subscript b in formula (II) is ranging from 3-30. For polyethylene glycol methyl ether-polylactide-lysine, the average molecular weight of polylactide block is ranging from 505-4982 and the average molecular weight of polyethylene glycol methyl ether is ranging from 1017-2992. Polyethylene glycol methyl ether-polylactide-lysine is prepared according to China patent application No. 2013000453. The average molecular weight of different blocks is determined by mass spectrum analysis with molecular weight of the materials.

In Examples 1-7, pharmaceutical component of pharmaceutical component containing docetaxel is micelles, which is prepared by film hydration method. The steps of method include:

(1) Docetaxel and polyethylene glycol methyl ether-polylactide-lysine are weighted respectively according to the different feeding ratios (see Table 5).

(2) The above raw materials (which include docetaxel and polyethylene glycol methyl ether-polylactide-lysine) are disposed into a container, and an organic solvent is added into container until the raw materials dissolved completely, in which the organic solvent includes ethanol, acetonitrile or the like. The container is rotated and evaporated under 30-50° C. for 2 hours until the organic solvent was evaporated to dryness. The remaining organic solvent is dried in vacuo at 10-60° C. and is performed more than 12 hours, so as to the polymeric mixed film of docetaxel-containing can be obtained.

(3) The polymer mixed film is disposed in a water bath with a temperature at 40-60° C. until the polymer mixed film becomes the transparent. Then, the preheated ultrapure water, physiological saline, or phosphate buffer with same temperature as the polymer mixed film is added into the polymer mixed film (disposed in water bath) and is shaken and hydrated well. Thus, the transparent drug loading micellar solution is obtained.

(4) The drug loading micelle solution is filtered with 0.45 μm filter membrane to obtain micelles.

(5) The drug loading micelle is subjected to the lyophilization process without adding any excipient to obtain the solid freeze-dried powder.

The preparation method of the freeze-dried powder includes:

Step a: the temperature of a shelf is pre-cooling to 0° C. and a solution containing docetaxel micelles is disposed on a pre-cooled shelf to cool the temperature of the solution containing docetaxel micelles to below −45° C., so that the temperature of the solution containing docetaxel micelles is dropped to −45° C., and the temperature of the solution containing docetaxel micelles is maintained at −45° C. for 2-4 hours.

Step b: the vacuum pump is turned on and the shalf where the solution containing docetaxel micelles thereon is performed with vacuuming for 1-1.5 hours after the step a.

Step c: the temperature of the shalf is set from −45° C. to −25° C. and the temperature of the shalf is maintained more than 12 hours. The shalf with an ultimate vacuum is set at 0.013 Bar.

Step d: the temperature of the shalf is set from −25° C. to 0° C. and the temperature of the shalf is maintained more than 8 hours. The shalf with an ultimate vacuum is set at 0.013 Bar.

Step e: the temperature of the shalf is set from 0° C. to 5° C. and the temperature of the shalf is maintained more than 3 hours. The shalf with an ultimate vacuum is set at 0.013 Bar.

Step f: the temperature of the shalf is set from 5° C. to 20° C. After the temperature of the solution containing docetaxel micelles is reached at 20° C., and the temperature of the solution containing docetaxel micelles is maintained more than 4 hours. Then, the lyophilization process is finished and the freeze-dried powder with loose block can be obtained.

In addition, according to above steps, an additional step (6) to add an excipient to prepare a freeze-dried powder, and the steps as follows:

The excipient is added into the docetaxel micelle and the total weight of the excipient is not exceeding 5% of above step (1). The excipient and the docetaxel micelle are fully dissolved. Next, according to above step (5), the lyophilization process is performed to the mixture of the excipient and the docetaxel micelles to prepare the docetaxel freeze-dried powder. The excipient is selected from the group consisting of one or more of lactose, mannitol, dextran, glycine, and glucose.

In above preparation, the organic solvent is ethanol or acetonitrile in above step (2).

The role of excipients in the lyophilization process is to promote the solution which is difficult to be solidified, so as to the solid powder can be obtained. The various excipients can also improve the performance indicators such as appearance, shape, solubility, and stability of the docetaxel freeze-dried powder according to varying degree.

Examples 1-7 select the different feed ratios and the polyethylene glycol methyl ether-polylactide-lysine with different molecular weight, which is prepared in accordance with the above procedure to obtain the docetaxel freeze-dried powder. The amount of the drug loading is determined by HPLC and the average particle size of the solution which is redissolved is determined by dynamic light scattering, see Table 5.

TABLE 5 the measurement result for amount of the drug loading and particle size in different examples.

| Example | Polyethylene glycol methyl ether M.W. | Polylactide M.W. | Feed ration Docetaxel:carrier | Acutal drug loading (Docetaxel:carrier) | Average particele size (nm) |
|---|---|---|---|---|---|
| Example 1 | 1989 | 843 | 4:100 | 3.24:100 | 20.0 |
| Example 2 | 2010 | 1406 | 8:100 | 6.85:100 | 29.2 |
| Example 3 | 1998 | 1688 | 16:100 | 14.28:100 | 24.9 |
| Example 4 | 1973 | 1923 | 30:100 | 27.75:100 | 26.1 |
| Example 5 | 2033 | 3220 | 20:100 | 18.52:100 | 24.0 |
| Example 6 | 1017 | 505 | 10:100 | 8.90:100 | 26.9 |
| Example 7 | 2992 | 4982 | 6:100 | 5.26:100 | 26.5 |

Carrier: polyethylene glycol methyl ether-polylactide-lysine

In accordance with the ratio of 3 mg/ml concentration of docetaxel, the docetaxel freeze-dried powder and water are weighted respectively which is prepared by Examples 1-7. The above freeze-dried powder is fed into the water for injection, the physiological saline or glucose for injection. Next, the docetaxel freeze-dried powder is fully dissolved after shaking with 60 seconds, so as to the docetaxel freeze-dried powder indicates good solubility. The average particle size distribution of the solution (or called redissolved solution) with docetaxel freeze-dried powder is determined, and the particle size of the redissolved solution is ranging from 10-100 nm, an average particle size is ranging from 20-29.2 nm, as shown in Table 6. The redissolved solution is respectively observed at 15° C., 25° C., 30'C and under the normal indoor lighting condition every 2 hours, until the solution appears cloudy or the precipitation was found. The observation result shows that the end of the steady state of the redissolved solution. The results are shown in Table 6, which illustrate the docetaxel freeze-dried powder of the present invention has good stability.

TABLE 6 the test results for the average particle size and the stability for the redissolved soltion in different Examples

| Example | Redissolved solvent | Average particle size (nm) | Settling time (Hour) | | |
|---|---|---|---|---|---|
| | | | 15° C. | 25° C. | 30° C. |
| Example1 | Water for injection | 20.0 | 26 | 14 | 6 |
| Example 2 | 0.9% NaCl | 29.2 | 32 | 24 | 14 |
| Example 3 | 5.0% Glucose | 24.9 | 28 | 14 | 8 |
| Example 4 | 0.9% Nacl | 26.1 | 28 | 12 | 6 |
| Example 5 | Water for injection | 24.0 | 24 | 12 | 6 |
| Example 6 | Water for injection | 26.9 | 18 | 12 | 10 |
| Example 7 | Water for injection | 26.5 | 16 | 16 | 8 |

Stability Test:

The docetaxel micelles which is prepared from Examples 1-7 is diluted with water to obtain docetaxel concentration of about 3 mg/ml. The solution (docetaxel micelles diluted with water) is respectively observed at 15° C., 25° C., 30° C. and under the normal indoor lighting condition every 2 hours, until the solution appears cloudy or the precipitation was found. The observation result shows that the end of the steady state of the solution (docetaxel micelles diluted with water). The results are shown in Table 7.

TABLE 7 the stability test results in different Examples

| Example | Settling time (Hour) | | |
|---|---|---|---|
| | 15° C. | 25° C. | 30° C. |
| Example 1 | 26 | 12 | 6 |
| Example 2 | 32 | 22 | 14 |
| Example 3 | 28 | 16 | 8 |
| Example 4 | 28 | 14 | 6 |
| Example 5 | 24 | 12 | 6 |
| Example 6 | 18 | 14 | 10 |
| Example 7 | 16 | 16 | 8 |

Example 8

The physiological saline, the commercial docetaxel for injection (Taxotere) and the docetaxel micelle solution (prepared by the invention) are subjected to a tumor suppression test. The testing object is Balb/c mice with transplanted L7912 tumor strain. The administration route is intravenous administration, one time every three days, and administered continuously for 30 days. The drug concentration of Taxotere is same as docetaxel of 10 mg/kg of the present invention. The tumor volume in mice was measured twice every week, and the results as shown in Table 8. The results show that the tumor volume in mice with the saline drip is rapidly grown. The growing speed of the tumor volume in mice with the Taxotere drip can be controlled, but the tumor volume is still growing. The tumor volume in mice with the docetaxel of the invention is controlled and reduced quickly, as shown in Table 8. Accordingly, the docetaxel of the invention for the T cell leukemia tumor in mice has good inhibitory effect.

TABLE 8 the measurements result for the tumor volume in mice

| Time (day) | Physiological saline | | Commerical docetaxel for injection | | Docetaxel of the invention | |
|---|---|---|---|---|---|---|
| | Tumor volume (Mm³) | variance | Tumor volume (Mm³) | variance | Tumor volume (Mm³) | variance |
| 1 | 165.7 | 38.0 | 156.0 | 13.0 | 160.0 | 31.0 |
| 5 | 246.0 | 79.0 | 177.0 | 7.5 | 130.8 | 30.0 |
| 8 | 307.0 | 88.0 | 154.0 | 8.3 | 58.0 | 19.0 |
| 12 | 401.0 | 149.0 | 157.0 | 4.3 | 16.1 | 4.8 |

TABLE 8-continued the measurements result for the tumor volume in mice

| Time (day) | Physiological saline Tumor volume (Mm³) | variance | Commerical docetaxel for injection Tumor volume (Mm³) | variance | Docetaxel of the invention Tumor volume (Mm³) | variance |
|---|---|---|---|---|---|---|
| 15 | 466.0 | 124.0 | 175.0 | 3.8 | 8.8 | 1.9 |
| 19 | 552.0 | 90.0 | 178.0 | 7.3 | 3.2 | 1.9 |
| 22 | 642.0 | 79.6 | 187.9 | 13.9 | 1.8 | 1.1 |
| 26 | 707.9 | 44.9 | 226.7 | 27.5 | 1.6 | 1.4 |
| 30 | 861.3 | 110.7 | 305.2 | 52.0 | 2.6 | 1.8 |

Examples 9-15

In Examples 9-15, Docetaxel is anhydrous docetaxel (CAS: 114977-28-5), which is produced by Xi'an Tianfeng natural field Bio-Technique Co., Ltd.

In Examples 9-15, polyethylene glycol methyl ether-polylactide block copolymer with amino acid end groups is polyethylene glycol methyl ether-polylactide-aspartic acid, and the chemical formula of polyethylene glycol methyl ether-polylactide-aspartic acid as follows:

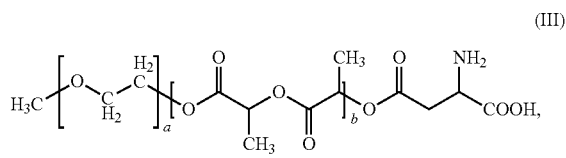

(III)

wherein the subscript a in formula (III) is ranging from 10-200, the subscript b in formula (III) is ranging from 3-30. For the polyethylene glycol methyl ether-polylactide-aspartic acid, the average molecular weight of polylactide block is ranging from 495-4996 and the average molecular weight of polyethylene-glycol methyl ether is ranging from 987-3020. Polyethylene glycol methyl ether-polylactide-aspartic acid is prepared according to China patent application No. 2013000453. The average molecular weight of the different blocks is determined by mass spectrum analysis with molecular weight of the materials.

In Examples 9-15, the pharmaceutical component of pharmaceutical component containing docetaxel is micelles, which is prepared by film hydration method. The steps of the method include:

(1) Docetaxel and polyethylene glycol methyl ether-polylactide-aspartic acid are weighted respectively according to different feed ratios (see Table 7).

(2) The above raw materials (which include docetaxel and polyethylene glycol methyl ether-polylactide-aspartic acid) are placed into a container, and an organic solvent is added into container until the raw materials dissolved completely, in which the organic solvent includes ethanol, acetonitrile or the like. The container is rotated and evaporated under 30-50° C. for 2 hours until the organic solvent was evaporated to dryness. The remaining organic solvent is dried in vacuo at 10-60° C. and is performed more than 12 hours, so as to the polymeric mixed film of docetaxel-containing can be obtained.

(3) The polymer mixed film is disposed in a water bath with a temperature at 40-60° until the polymer mixed film becomes the transparent. Then, pre-heated ultrapure water, physiological saline, or phosphate buffer with same temperature as that of the polymer mixed film is added into the polymer mixed film (disposed in water bath) and is shaken and hydrated well. Thus, the transparent drug loading micelle solution is obtained.

(4) The drug loading micelle solution is filtered with 0.45 μm filter membrane to obtain micelles.

(5) The drug loading micelle is subjected to lyophilization process without adding any excipient to obtain the solid freeze-dried powder.

The step of preparation method of the freeze-dried powder includes:

Step a: the temperature of a shelf is pre-cooling process to 0° C. and a solution containing docetaxel micelles is disposed on a pre-cooled shelf to cool the temperature of the solution containing docetaxel micelles to below −45° C., so that the solution temperature of the solution containing docetaxel micelles is dropped to −45° C., and the temperature of the solution containing docetaxel micelles is maintained at −45° C. for 2-4 hours.

Step b: the vacuum pump is turned on and the shalf where the solution containing docetaxel micelles thereon is performed with vacuuming for 1-1.5 hours after the step a.

Step c: the temperature of the shalf is set from −45° C. to −25° C. and the temperature of the shalf is maintained more than 12 hours. The shalf with an ultimate vacuum is set at 0.013 Bar.

Step d: the temperature of the shalf is set from −25° C. to 0° C. and the temperature of the shalf is maintained more than 8 hours. The shalf with an ultimate vacuum is set at 0.013 Bar.

Step e: the temperature of the shalf is set from 0° C. to 5° C. and the temperature of the shalf is maintained more than 3 hours. The shalf with an ultimate vacuum is set at 0.013 Bar.

Step f: the temperature of the shalf is set from 5° C. to 20° C. After the temperature of the solution containing docetaxel micelles is reached at 20° C., and the temperature of the product solution containing docetaxel micelles is maintained more than 4 hours. Then, the lyophilization process is finished and the freeze-dried powder with loose block can be obtained.

In addition, according to above steps, an additional step (6) to add an excipient to prepare a freeze-dried powder includes:

The excipient is added into the docetaxel micelle and the total weight of the excipient is not exceeding 5% of above step (1), and the excipient and the docetaxel micelle are fully dissolved. Next, according to above step (5), the lyophilization process is performed to the mixture of the excipient and the docetaxel micelle to prepare the docetaxel freeze-dried powder. The excipient is selected from the group consisting of one or more of lactose, mannitol, dextran, glycine, and glucose.

In above preparation, the organic solvent is ethanol or acetonitrile in above step (2).

The role of excipients in the lyophilization process is to promote the solution which is difficult to be solidified, so as to the solid powder can be obtained. The various excipients can also improve the performance indicators such as appearance, shape, solubility, and stability of the docetaxel freeze-dried powder according to varying degree.

Examples 9-15 select the different feed ratios and the polyethylene glycol methyl ether-polylactide-aspartic acid with different molecular weight, which is prepared in accordance with the above procedure to obtain the docetaxel freeze-dried powder. The amount of the drug loading is determined by HPLC and the average particle size of the solution which is redissolved is determined by dynamic light scattering, as shown in Table 9.

TABLE 9 the measurement result for amount of the drug loading and particle size in different examples.

| Example | Polyethylene glycol methyl ether M.W. | Polylactide M.W. | Feed ratio Docetaxel:carrier | Acutal drug loading (Docetaxel:carrier) | Average particele size (nm) |
|---|---|---|---|---|---|
| Example 9 | 2018 | 855 | 4:100 | 3.21:100 | 20.6 |
| Example 10 | 2020 | 1438 | 8:100 | 6.22:100 | 28.1 |
| Example 11 | 1981 | 1660 | 16:100 | 13.98:100 | 25.5 |
| Example 12 | 2033 | 1968 | 30:100 | 26.48:100 | 26.8 |
| Example 13 | 1988 | 3211 | 20:100 | 17.87:100 | 25.3 |
| Example 14 | 987 | 495 | 10:100 | 8.56:100 | 28.1 |
| Example 15 | 3020 | 4996 | 6:100 | 4.67:100 | 26.2 |

Carrier = polyethylene glycol methyl ether-polylactide-aspartate acid

In accordance with the ratio of 3 mg/ml concentration of docetaxel, the docetaxel freeze-dried powder and water are weighted respectively which is prepared by Examples 9-15. The above freeze-dried powder is fed into the water for injection, the physiological saline or glucose for injection. Next, the docetaxel freeze-dried powder is fully dissolved after shaking about 60 seconds. The docetaxel freeze-dried powder indicates good solubility. The average particle size distribution of the solution (or called redissolved solution) with docetaxel freeze-dried powder is determined, and the particle size of the redissolved solution is ranging from 10-100 nm, an average particle size is ranging from 20-29.2 nm, as shown in Table 10. The redissolved solution is respectively observed at 15° C., 25° C., 30° C. and under the normal indoor lighting condition every 2 hours, until the solution appears cloudy or the precipitation was found. The observation result shows that the end of the steady state of the redissolved solution. The results are shown in Table 10, which illustrate the docetaxel freeze-dried powder of the present invention has good stability.

TABLE 10 the test results for the average particle size and the stability for the redissolved soltion in different Examples

| Example | Redissolved solvent | Average particle size (nm) | Settling time (Hour) | | |
|---|---|---|---|---|---|
| | | | 15° C. | 25° C. | 30° C. |
| Example 9 | Water for injection | 20.6 | 26 | 14 | 6 |
| Example 10 | 0.9% NaCl | 28.1 | 32 | 24 | 14 |
| Example 11 | 5.0% Glucose | 25.5 | 28 | 14 | 8 |
| Example 12 | 0.9% NaCl | 26.8 | 28 | 12 | 6 |
| Example 13 | Water for injection | 25.3 | 24 | 12 | 6 |
| Example 14 | Water for injection | 28.1 | 18 | 12 | 10 |
| Example 15 | Water for injection | 26.2 | 16 | 16 | 8 |

Stability Test

The docetaxel micelles which is prepared from Examples 9-15 is diluted with water to obtain docetaxel concentration of about 3 mg/ml. The solution (docetaxel micelles diluted with water) is respectively observed at 15° C., 25° C., 30° C. and under the normal indoor lighting condition every 2 hours, until the solution appears cloudy or the precipitation was found. The observation result shows that the end of the steady state of the solution (docetaxel micelles diluted with water). The results are shown in Table 11.

TABLE 11 the stability test results in different Examples

| | Settling time (Hour) | | |
|---|---|---|---|
| Example | 15° C. | 25° C. | 30° C. |
| Example 9 | 26 | 12 | 8 |
| Example 10 | 32 | 20 | 14 |
| Example 11 | 28 | 14 | 8 |
| Example 12 | 28 | 14 | 6 |
| Example 13 | 24 | 12 | 6 |
| Example 14 | 18 | 14 | 10 |
| Example 15 | 16 | 16 | 8 |

Example 16

The physiological saline, the commercial docetaxel for injection (Taxotere) and the docetaxel micelle solution (prepared by the invention) are subjected to a tumor suppression test. The testing object is Balb/c mice with transplanted L7912 tumor strain. The administration route is intravenous administration, one time every three days, and administered continuously for 30 days. The drug concentration of Taxotere is same as docetaxel of 10 mg/kg of the present invention. The tumor volume in mice was measured twice every week, and the results as shown in Table 12. The results show that the tumor volume in mice with the saline drip is rapidly grown. The growing speed of the tumor volume in mice with the Taxotere drip can be controlled, but the tumor volume is still growing. The tumor volume in mice with the docetaxel of the invention is controlled and reduced quickly, as shown in Table 12. Accordingly, the docetaxel of the invention for the T cell leukemia tumor in mice has good inhibitory effect.

TABLE 12 the measurements result for the tumor volume in mice

| Time (day) | Physiological saline Tumor volume (Mm³) | variance | Commerical docetaxel for injection Tumor volume (Mm³) | variance | Docetaxel of the invention Tumor volume (Mm³) | variance |
|---|---|---|---|---|---|---|
| 1  | 165.7 | 38.0  | 156.0 | 13.0 | 157.1 | 28.0 |
| 5  | 246.0 | 79.0  | 177.0 | 7.5  | 127.0 | 31.5 |
| 8  | 307.0 | 88.0  | 154.0 | 8.3  | 56.8  | 16.0 |
| 12 | 401.0 | 149.0 | 157.0 | 4.3  | 18.0  | 6.0  |
| 15 | 466.0 | 124.0 | 175.0 | 3.8  | 8.8   | 2.0  |
| 19 | 552.0 | 90.0  | 178.0 | 7.3  | 4.1   | 1.8  |
| 22 | 642.0 | 79.6  | 187.9 | 13.9 | 1.6   | 0.9  |
| 26 | 707.9 | 44.9  | 226.7 | 27.5 | 1.9   | 1.0  |
| 30 | 861.3 | 110.7 | 305.2 | 52.0 | 2.8   | 2.0  |

Examples 17-23

Docetaxel is anhydrous docetaxel (CAS: 114977-28-5), which is produced by Xi'an Tianfeng natural field Bio-Technique Co., Ltd.

In Examples 17-23, polyethylene glycol methyl ether-polylactide block copolymer with amino acid end groups is polyethylene glycol methyl ether-polylactide-glutamic acid, and the chemical formula of polyethylene glycol methyl ether-polylactide-glutamic acid as follows:

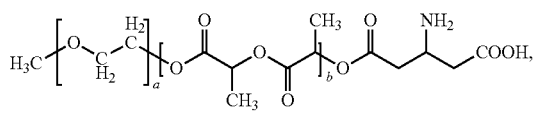

(IV)

wherein the subscript a in formula (IV) is ranging from 10-200, the subscript b in formula (IV) is ranging from 3-30. For polyethylene glycol methyl ether-polylactide-glutamic acid, the average molecular weight of polylactide block is ranging from 504-4985 and the average molecular weight of polyethylene glycol methyl ether is ranging from 1003-3015. Polyethylene glycol methyl ether-polylactide-glutamic acid is prepared according to China patent application No. 2013000453. The average molecular weight of different blocks is determined by mass spectrum analysis with molecular weight of the materials.

In Examples 17-23, the pharmaceutical component of pharmaceutical component containing docetaxel is micelles, which is prepared by film hydration method. The steps of the method include:

(1) Docetaxel and polyethylene glycol methyl ether-polylactide-glutamic acid are weighted respectively according to different feed ratios (see Table 13).
(2) The above raw materials (which include docetaxel and polyethylene glycol methyl ether-polylactide-glutamic acid) are disposed into a container, and an organic solvent is added into container until the raw materials dissolved completely, in which the organic solvent includes ethanol, acetonitrile and the like. The container is rotated and evaporated under 30-50° C. for 2 hours until the organic solvent was evaporated to dryness. The remaining organic solvent is dried in vacuo at 10-60° C. and is performed more than 12 hours, so as to the polymeric mixed film of docetaxel-containing can be obtained.
(3) The polymer mixed film is disposed in a water bath with a temperature at 40-60° C. until the polymer mixed film becomes the transparent. Then, preheated ultrapure water, physiological saline, or phosphate buffer with same temperature as the polymer mixed film is added into the polymer mixed film (disposed in water bath) and is shaken and hydrated well. Thus, the transparent drug loading micellar solution is obtained.
(4) The drug loading micelle solution is filtered with 0.45 μm filter membrane to obtain micelles.
(5) The drug loading micelle is subjected to lyophilization process without adding any excipient to obtain the solid freeze-dried powder.

The preparation method of the freeze-dried powder as follows:

Step a: the temperature of a shelf is pre-cooling process to 0° C. and a solution containing docetaxel micelles is disposed on a pre-cooled shelf to cool the temperature of the solution containing docetaxel micelles to below −45° C., so that the temperature of the solution containing docetaxel micelles is dropped to −45° C., and the temperature of the solution containing docetaxel micelles is maintained at −45° C. for 2-4 hours.

Step b: the vacuum pump is turned on and the shalf where the solution containing docetaxel micelles thereon is performed with vacuuming for 1-1.5 hours after the step a.

Step c: the temperature of the shalf is set from −45° C. to −25° C. and the temperature of the shalf is maintained more than 12 hours. The shalf with an ultimate vacuum is set at 0.013 Bar.

Step d: the temperature of the shalf is set from −25° C. to 0° C. and the temperature of the shalf is maintained more than 8 hours. The shalf with an ultimate vacuum is set at 0.013 Bar.

Step e: the temperature of the shalf is set from 0° C. to 5° C. and the temperature of the shalf is maintained more than 3 hours. The shalf with an ultimate vacuum is set at 0.013 Bar.

Step f: the temperature of the shalf is set from 5° C. to 20° C. After the temperature of the solution containing docetaxel micelles is reached at 20° C., the temperature of the solution containing docetaxel micelles is maintained more than 4 hours. Then, the lyophilization process is finished and the freeze-dried powder with loose block can be obtained.

In addition, according to above steps, an additional step (6) to add an excipient to prepare a freeze-dried powder as follows:

The excipient is added into the docetaxel micelle and the total weight of the excipient is not exceeding 5% of above step (1), and the excipient and the docetaxel micelle are fully dissolved. Next, according to above step (5), the lyophilization process is performed to the mixture of the excipient and the docetaxel micelle to prepare the docetaxel freeze-dried powder. The excipient is selected from the group consisting of one or more of lactose, mannitol, dextran, glycine, and glucose.

In above preparation, the organic solvent is ethanol or acetonitrile in above step (2).

The role of excipients in the lyophilization process is to promote the solution which is difficult to be solidified, so as to the solid powder can be obtained. The various excipients can also improve the performance indicators such as appearance, shape, solubility, and stability of the docetaxel freeze-dried powder according to varying degree.

Examples 17-23 select the different feed ratios and the polyethylene glycol methyl ether-polylactide-glutamic acid with different molecular weight, which is prepared in accordance with the above procedure to obtain the docetaxel freeze-dried powder. The amount of the drug loading is determined by HPLC and the average particle size of the solution which is redissolved is determined by dynamic light scattering and as shown in Table 13.

TABLE 13 the measurement result for amount of drug loading and particle size in different examples.

| Example | Polyethylene glycol methyl ether M.W. | Polylactide M.W. | Feed ratio Docetaxel:carrier | Acutal drug loading (Docetaxel:carrier) | Average particele size (nm) |
|---|---|---|---|---|---|
| Example 17 | 1989 | 842 | 4:100 | 3.43:100 | 21.5 |
| Example 18 | 1998 | 1419 | 8:100 | 6.67:100 | 28.9 |
| Example 19 | 2009 | 1685 | 16:100 | 12.55:100 | 27.6 |
| Example 20 | 1996 | 1905 | 30:100 | 26.78:100 | 26.2 |
| Example 21 | 2014 | 3256 | 20:100 | 17.85:100 | 25.3 |
| Example 22 | 1003 | 504 | 10:100 | 8.90:100 | 27.2 |
| Example 23 | 3015 | 4985 | 6:100 | 4.20:100 | 26.6 |

Carrier = polyethylene glycol methyl ether-polylactide-glutamic acid

In accordance with the ratio of 3 mg/ml concentration of docetaxel, the docetaxel freeze-dried powder and water are weighted respectively which is prepared by Examples 17-23. The above freeze-dried powder is fed into the water for injection, the physiological saline or glucose for injection. Next, the docetaxel freeze-dried powder is fully dissolved after shaking with 60 seconds, so as to the docetaxel freeze-dried powder indicates good solubility. The average particle size distribution of the solution (or called redissolved solution) with docetaxel freeze-dried powder is determined, and the particle size of the redissolved solution is ranging from 10-100 nm, an average particle size is ranging from 20-29.2 nm, as shown in Table 14. The redissolved solution is respectively observed at 15° C., 25° C., 30° C. and under the normal indoor lighting condition every 2 hours, until the solution appears cloudy or the precipitation was found. The observation result shows that the end of the steady state of the redissolved solution. The results are shown in Table 14, which illustrate the docetaxel freeze-dried powder of the present invention has good stability.

TABLE 14 the test results for the average particle size and the stability for the redissolved soltion in different Examples

| Example | Redissolved solvent | Average particle size (nm) | Settling time (Hour) 15° C. | 25° C. | 30° C. |
|---|---|---|---|---|---|
| Example 17 | Water for injection | 21.5 | 26 | 14 | 6 |
| Example 18 | 0.9% NaCl | 28.9 | 32 | 24 | 14 |
| Example 19 | 5.0% Glucose | 27.6 | 28 | 14 | 8 |
| Example 20 | 0.9% NaCl | 26.2 | 28 | 12 | 6 |
| Example 21 | Water for injection | 25.3 | 24 | 12 | 6 |
| Example 22 | Water for injection | 27.2 | 18 | 12 | 10 |
| Example 23 | Water for injection | 26.6 | 16 | 16 | 8 |

Stability Test:

The docetaxel micelles which is prepared from Examples 17-23 is diluted with water to obtain docetaxel concentration of about 3 mg/ml. The solution (docetaxel micelles diluted with water) is respectively observed at 15° C., 25° C., 30° C. and under the normal indoor lighting condition every 2 hours, until the solution appears cloudy or the precipitation was found. The observation result shows that the end of the steady state of the solution (docetaxel micelles diluted with water). The results are shown in Table 15.

TABLE 5 the stability test results in different Examples

| Example | Settling time (Hour) 15° C. | 25° C. | 30° C. |
|---|---|---|---|
| Example 17 | 26 | 12 | 6 |
| Example 18 | 32 | 24 | 12 |
| Example 19 | 28 | 14 | 8 |
| Example 20 | 28 | 14 | 6 |
| Example 21 | 24 | 12 | 8 |
| Example 22 | 18 | 14 | 10 |
| Example 23 | 16 | 16 | 8 |

Example 24

The physiological saline, the commercial docetaxel for injection (Taxotere) and the docetaxel micelle solution (prepared by the invention) are subjected to a tumor suppression test. The testing object is Balb/c mice with transplanted L7912 tumor strain. The administration route is intravenous administration, one time every three days, and administered continuously for 30 days. The drug concentration of Taxotere is same as docetaxel of 10 mg/kg of the present invention. The tumor volume in mice was measured twice every week, and the results as shown in Table 16. The results show that the tumor volume in mice with the saline drip is rapidly grown. The growing speed of the tumor volume in mice with the Taxotere drip can be controlled, but the tumor volume is still growing. The tumor volume in mice with the docetaxel of the invention is controlled and reduced quickly, as shown in Table 16. Accordingly, the docetaxel of the invention for the T cell leukemia tumor in mice has good inhibitory effect.

TABLE 16 the measurements result for the tumor volume in mice

| Time (day) | Physiological saline Tumor volume (Mm³) | variance | Commercial docetaxel for injection Tumor volume (Mm³) | variance | Docetaxel of the invention Tumor volume (Mm³) | variance |
|---|---|---|---|---|---|---|
| 1 | 165.7 | 38.0 | 156.0 | 13.0 | 158.0 | 22.0 |
| 5 | 246.0 | 79.0 | 177.0 | 7.5 | 128.1 | 31.1 |
| 8 | 307.0 | 88.0 | 154.0 | 8.3 | 54.7 | 18.8 |
| 12 | 401.0 | 149.0 | 157.0 | 4.3 | 18.0 | 5.1 |
| 15 | 466.0 | 124.0 | 175.0 | 3.8 | 7.8 | 2.2 |
| 19 | 552.0 | 90.0 | 178.0 | 7.3 | 3.0 | 1.2 |
| 22 | 642.0 | 79.6 | 187.9 | 13.9 | 1.6 | 0.9 |
| 26 | 707.9 | 44.9 | 226.7 | 27.5 | 1.7 | 1.4 |
| 30 | 861.3 | 110.7 | 305.2 | 52.0 | 2.6 | 2.0 |

Examples 25-31

Docetaxel is anhydrous docetaxel (CAS: 114977-28-5), which is produced by Xi'an Tianfeng natural field Bio-Technique Co., Ltd.

In Examples 25-31, polyethylene glycol methyl ether-polylactide block copolymer with amino acid end groups is polyethylene glycol methyl ether-polylactide-phenylalanine, and the chemical formula of polyethylene glycol methyl ether-polylactide-phenylalanine as follows

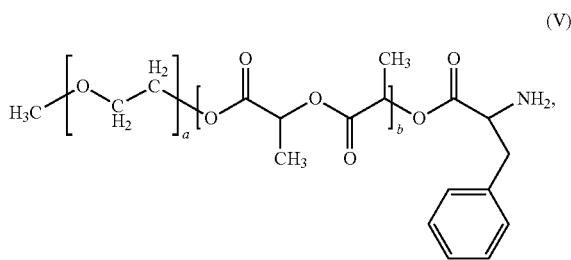

(V)

wherein the subscript a in formula (V) is ranging from 10-200, the subscript b in formula (V) is ranging from 3-30. For polyethylene glycol methyl ether-polylactide-phenylalanine, the average molecular weight of polylactide block is ranging from 502-4962 and the average molecular weight of polyethylene glycol methyl ether is ranging from 998-2998. Polyethylene glycol methyl ether-polylactide-phenylalanine is prepared according to China patent application No. 2013000453. The average molecular weight of different blocks is determined by mass spectrum analysis with molecular weight of the materials.

In Examples 25-31, the pharmaceutical component of pharmaceutical component containing docetaxel is micelles, which is prepared by a film hydration method. The steps of the method include:
(1) Docetaxel and polyethylene glycol methyl ether-polylactide-phenylalanine are weighted respectively according to different feed ratios (see Table 17).
(2) The above raw materials (which include docetaxel and polyethylene glycol methyl ether-polylactide-phenylalanine) are disposed into a container, and an organic solvent is added into container until the raw materials dissolved completely, in which the organic solvent includes ethanol, acetonitrile and the like. The container is rotated and evaporated under 30-50° C. for 2 hours until the organic solvent was evaporated to dryness. The remaining organic solvent is dried in vacuo at 10-60° C. and is performed more than 12 hours, so as to the polymeric mixed film of docetaxel-containing can be obtained.
(3) The polymer mixed film is disposed in a water bath with a temperature at 40-60° C. until the polymer mixed film becomes the transparent. Then, preheated ultrapure water, physiological saline, or phosphate buffer with same temperature as the polymer mixed film is added into the polymer mixed film (disposed in water bath) and is shaken and hydrated well. Thus, the transparent drug loading micellar solution is obtained.
(4) The drug loading micelle solution is filtered with 0.45 μm filter membrane to obtain micelles.
(5) The drug loading micelle is subjected to lyophilization process without adding any excipient to obtain the solid freeze-dried powder.

The preparation method of the freeze-dried powder as follows:
Step a: the temperature of a shelf is pre-cooling to 0° C. and a solution containing docetaxel micelles is disposed on a pre-cooled shelf to cool the temperature of the solution containing docetaxel micelles to below −45° C., so that the solution temperature of the solution containing docetaxel micelles is dropped to −45° C., and the temperature of the solution containing docetaxel micelles is maintained at −45° C. for 2-4 hours.
Step b: the vacuum pump is turned on and the shalf where the solution containing docetaxel micelles thereon is performed with vacuuming for 1-1.5 hours after the step a.
Step c: the temperature of the shalf is set from −45° C. to −25° C. and the temperature of the shalf is maintained more than 12 hours. The shalf with an ultimate vacuum is set at 0.013 Bar.
Step d: the temperature of the shalf is set from −25° C. to 0° C. and the temperature of the shalf is maintained more than 8 hours. The shalf with an ultimate vacuum is set at 0.013 Bar.
Step e: the temperature of the shalf is set from 0° C. to 5° C. and the temperature of the shalf is maintained more than 3 hours. The shalf with an ultimate vacuum is set at 0.013 Bar.
Step f: the temperature of the shalf is set from 5° C. to 20° C. After the temperature of the solution containing docetaxel micelles is reached at 20° C., and the temperature of the solution containing docetaxel micelles is maintained more than 4 hours. Then, the lyophilization process is finished and the freeze-dried powder with loose block can be obtained.

In addition, according to above steps, an additional step (6) to add an excipient to prepare a freeze-dried powder as follows:
The excipient is added into the docetaxel micelle and the total weight of the excipient is not exceeding 5% of above step (1), and the excipient and the docetaxel micelle are fully dissolved. Next, according to above step (5), the lyophilization process is performed to the mixture of the excipient and the docetaxel micelle to prepare the docetaxel freeze-dried powder. The excipient is selected from the group consisting of one or more of lactose, mannitol, dextran, glycine, and glucose.

In above preparation, the organic solvent is ethanol or acetonitrile in above step (2).

The role of excipients in the lyophilization process is to promote the solution which is difficult to be solidified, so as to the solid powder can be obtained. The various excipients can also improve the performance indicators such as appearance, shape, solubility, and stability of the docetaxel freeze-dried powder according to varying degree.

Examples 25-31 select the different feed ratios and the polyethylene glycol methyl ether-polylactide-phenylalanine with different molecular weight, which is prepared in accordance with the above procedure to obtain the docetaxel freeze-dried powder. The amount of the drug loading is determined by HPLC and the average particle size of the solution which is redissolved is determined by dynamic light scattering, as shown in Table 17.

TABLE 17 the measured amount of the drug loading and particle size in different examples

| Example | Polyethylene glycol methyl ether M.W. | Polylactide M.W. | Feed ratio Docetaxel:carrier | Acutal drug loading (Docetaxel:carrier) | Average particele size (nm) |
|---|---|---|---|---|---|
| Example 25 | 1996 | 847 | 4:100 | 3.57:100 | 18.5 |
| Example 26 | 2008 | 1420 | 8:100 | 5.42:100 | 22.6 |
| Example 27 | 1989 | 1678 | 16:100 | 15.02:100 | 23.5 |
| Example 28 | 1993 | 1909 | 30:100 | 25.76:100 | 24.2 |
| Example 29 | 2013 | 3230 | 20:100 | 16.98:100 | 24.7 |
| Example 30 | 998 | 502 | 10:100 | 8.46:100 | 24.1 |
| Example 31 | 2988 | 4962 | 6:100 | 4.42:100 | 24.2 |

Carrier: polyethylene glycol methyl ether-polylactide-phenylalanine

In accordance with the ratio of 3 mg/ml concentration of docetaxel, the docetaxel freeze-dried powder and water are weighted respectively which is prepared by Examples 25-31. The above freeze-dried powder is fed into the water for injection, the physiological saline or glucose for injection. Next, the docetaxel freeze-dried powder is fully dissolved after shaking with 60 seconds, so as to the docetaxel freeze-dried powder indicates good solubility. The average particle size distribution of the solution (or called redissolved solution) with docetaxel freeze-dried powder is determined, and the particle size of the redissolved solution is ranging from 10-100 nm, an average particle size is ranging from 20-29.2 nm, as shown in Table 18. The redissolved solution is respectively observed at 15° C., 25° C., 30° C. and under the normal indoor lighting condition every 2 hours, until the solution appears cloudy or the precipitation was found. The observation result shows that the end of the steady state of the redissolved solution. The results are shown in Table 18, which illustrate the docetaxel freeze-dried powder of the present invention has good stability.

TABLE 18 the test results for the average particle size and the stability for the redissolved soltion in different Examples

| Example | Redissolved solvent | Average particle size (nm) | Settling time (Hour) | | |
|---|---|---|---|---|---|
| | | | 15° C. | 25° C. | 30° C. |
| Example 25 | Water for injection | 18.5 | 26 | 14 | 6 |
| Example 26 | 0.9% NaCl | 22.6 | 32 | 24 | 14 |
| Example 27 | 5.0% Glucose | 23.5 | 28 | 14 | 8 |
| Example 28 | 0.9% NaCl | 24.2 | 28 | 12 | 6 |
| Example 29 | Water for injection | 24.7 | 24 | 12 | 6 |
| Example 30 | Water for injection | 24.1 | 18 | 12 | 10 |
| Example 31 | Water for injection | 24.2 | 16 | 16 | 8 |

Stability Test:

The docetaxel micelles which is prepared from Examples 25-31 is diluted with water to obtain docetaxel concentration of about 3 mg/ml. The solution (docetaxel micelles diluted with water) is respectively observed at 15° C., 25° C., 30° C. and under the normal indoor lighting condition every 2 hours, until the solution appears cloudy or the precipitation was found. The observation result shows that the end of the steady state of the solution (docetaxel micelles diluted with water). The results are shown in Table 19.

TABLE 19 the stability test results in different Examples

| Example | Settling time (Hour) | | |
|---|---|---|---|
| | 15° C. | 25° C. | 30° C. |
| Example 25 | 26 | 12 | 6 |
| Example 26 | 32 | 18 | 12 |
| Example 27 | 28 | 14 | 10 |
| Example 28 | 28 | 14 | 8 |
| Example 29 | 24 | 12 | 8 |
| Example 30 | 18 | 14 | 10 |
| Example 31 | 16 | 16 | 8 |

Example 32

The physiological saline, the commercial docetaxel for injection (Taxotere) and the docetaxel micelle solution (prepared by the invention) are subjected to a tumor suppression test. The testing object is Balb/c mice with transplanted L7912 tumor strain. The administration route is intravenous administration, one time every three days, and administered continuously for 30 days. The drug concentration of Taxotere is same as docetaxel of 10 mg/kg of the present invention. The tumor volume in mice was measured twice every week, and the results as shown in Table 20. The results show that the tumor volume in mice with the saline drip is rapidly grown. The growing speed of the tumor volume in mice with the Taxotere drip can be controlled, but the tumor volume is still growing. The tumor volume in mice with the docetaxel of the invention is controlled and reduced quickly, as shown in Table 20. Accordingly, the docetaxel of the invention for the T cell leukemia tumor in mice has good inhibitory effect.

TABLE 20 the measurements result for the tumor volume in mice

| Time (day) | Physiological saline | | Commerical docetaxel for injection | | Docetaxel of the invention | |
|---|---|---|---|---|---|---|
| | Tumor volume (Mm$^3$) | variance | Tumor volume (Mm$^3$) | variance | Tumor volume (Mm$^3$) | variance |
| 1 | 165.7 | 38.0 | 156.0 | 13.0 | 156.0 | 32.0 |
| 5 | 246.0 | 79.0 | 177.0 | 7.5 | 127.0 | 31.0 |
| 8 | 307.0 | 88.0 | 154.0 | 8.3 | 57.0 | 17.0 |
| 12 | 401.0 | 149.0 | 157.0 | 4.3 | 17.0 | 5.0 |

TABLE 20-continued the measurements result for the tumor volume in mice

| Time (day) | Physiological saline | | Commerical docetaxel for injection | | Docetaxel of the invention | |
|---|---|---|---|---|---|---|
| | Tumor volume (Mm³) | variance | Tumor volume (Mm³) | variance | Tumor volume (Mm³) | variance |
| 15 | 466.0 | 124.0 | 175.0 | 3.8 | 8.3 | 1.7 |
| 19 | 552.0 | 90.0 | 178.0 | 7.3 | 2.7 | 1.4 |
| 22 | 642.0 | 79.6 | 187.9 | 13.9 | 1.4 | 0.9 |
| 26 | 707.9 | 44.9 | 226.7 | 27.5 | 1.9 | 1.4 |
| 30 | 861.3 | 110.7 | 305.2 | 52.0 | 2.9 | 2.2 |

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A pharmaceutical composition containing docetaxel, comprising the pharmaceutical composition includes docetaxel and polyethylene glycol methyl ether-polylactide block copolymer with amino acid end groups, wherein the chemical formula of polyethylene glycol methyl ether-polylactide block copolymer with amino acid end groups is

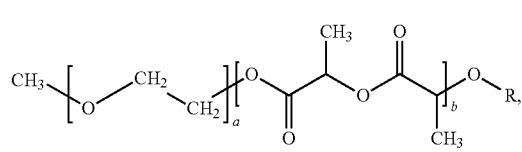

wherein R is an amino acid, the chemical formula of the amino acid R is

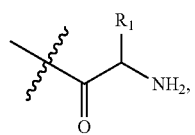

and the functional group R₁ is PhCH₂ or (CH₂)₃NHC(NH)NH₂, a is ranging from 10-200, b is ranging from 3-30, the average molecular weight of polyethylene glycol methyl ether is 998~2998 and the average molecular weight of polylactide block is 502~4962.

2. The pharmaceutical composition containing docetaxel according to claim 1, wherein the pharmaceutical composition is a freeze-dried powder preparation agent.

3. The pharmaceutical composition containing docetaxel according to claim 2, wherein the average particle size in a redissolved solution of the freeze-dried powder preparation agent is ranging from 20-29.2 nm.

4. The pharmaceutical composition containing docetaxel according to claim 2, wherein the freeze-dried powder is prepared by a lyophilization, and the steps of lyophilization include:

Step a: the temperature of a shelf is pre-cooling to 0° C. and a solution containing docetaxel micelles is deposed on the pre-cooled shelf to cool the temperature of the solution containing docetaxel micelles to below −45° C., so that the temperature of the solution containing docetaxel micelles is dropped to −45° C., and the temperature of the solution containing docetaxel micelles is maintained at −45° C. for 2-4 hours;

Step b: turning on a vacuum pump and vacuuming for 1-1.5 hours after the step a;

Step c: setting a temperature of the shalf from −45° C. to −25° C., and the temperature of the shelf is maintained more than 12 hours, and setting the shelf with an ultimate vacuum at 0.013 Bar;

Step d: setting the temperature of the shelf from −25° C. to 0° C., and the temperature of the shelf is maintained more than 8 hours and setting the vacuum pump with the ultimate vacuum at 0.013 Bar;

Step e: setting a temperature of the shelf from 0° C. to 5° C., and the temperature of the shelf is maintained more than 3 hours and setting the vacuum pump with the ultimate vacuum at 0.013 Bar; and Step f: setting a temperature of the shelf from 5° C. to 20° C. after the temperature of the solution containing docetaxel micelles is reached at 20° C., and the temperature of the solution containing docetaxel micelles is maintained at 20° C. more than 4 hours, whereby, the lyophilization process is finished and a freeze-dried powder with loose block is to be obtained.

5. The pharmaceutical composition containing docetaxel according to claim 1, wherein the pharmaceutical composition is micelles which is prepared by a film hydration method, and the method includes: (1) weighting docetaxel and polyethylene glycol methyl ether-polylactide block copolymer with an amino acid end group respectively according to different feed ratios; (2) disposing docetaxel and polyethylene glycol methyl ether-polylactide block copolymer with an amino acid end group into a container, and an organic solvent is added into container until the docetaxel and polyethylene glycol methyl ether-polylactide block copolymer with an amino acid end group dissolved completely; (3) rotating and evaporating the container under 30-50° C. for 2 hours until the organic solvent was evaporated to dryness and drying the remaining organic solvent is dried in vacuo at 10-60° C. for more than 12 hours, so as to a polymeric mixed film of docetaxel-containing is obtained; and (4) disposing the polymer mixed film in a water bath with a temperature at 40-60° C. until the polymer mixed film becomes the transparent, a preheated ultrapure water, physiological saline, or phosphate buffer with same temperature as the polymer mixed film is added into the polymer mixed film and is shaken and hydrated well to obtain a transparent drug loading micellar solution.

* * * * *